United States Patent [19]
Der Ovanesian

[11] Patent Number: 5,840,080
[45] Date of Patent: Nov. 24, 1998

[54] HOT OR COLD APPLICATOR WITH INNER ELEMENT

[76] Inventor: Mary Der Ovanesian, 6650 Coolidge St., Hollywood, Fla. 33024

[21] Appl. No.: 689,899

[22] Filed: Aug. 15, 1996

[51] Int. Cl.$^6$ ........................................................ A61F 7/00
[52] U.S. Cl. .............................. 607/114; 607/96; 607/112; 62/530
[58] Field of Search ........................ 607/96–114; 62/530; 126/204; 383/901; 165/46

[56] References Cited

U.S. PATENT DOCUMENTS

| | | | |
|---|---|---|---|
| 3,885,403 | 5/1975 | Spencer | 62/530 |
| 3,951,127 | 4/1976 | Watson et al. | 607/114 |
| 4,324,111 | 4/1982 | Edwards | 62/457 |
| 4,462,224 | 7/1984 | Danshee et al. | 62/530 |
| 4,530,220 | 7/1985 | Nambu et al. | 62/530 |
| 4,573,447 | 3/1986 | Thrash et al. | 607/114 |
| 4,576,169 | 3/1986 | Williams | 128/402 |
| 4,592,358 | 6/1986 | Westplate | 128/402 |
| 4,676,247 | 6/1987 | Vancleve | 128/402 |
| 4,856,651 | 8/1989 | Francis, Jr. | 607/114 |
| 4,962,761 | 10/1990 | Golden | 607/104 |
| 5,179,944 | 1/1993 | McSgmytz | 607/114 |
| 5,265,669 | 11/1993 | Schneider | 165/46 |
| 5,304,216 | 4/1994 | Wallace | 607/112 |
| 5,314,005 | 5/1994 | Dobry | 165/10 |
| 5,395,400 | 3/1995 | Stafford et al. | 607/114 |
| 5,486,206 | 1/1996 | Avery | 607/114 |
| 5,534,020 | 7/1996 | Cheney, III et al. | 607/114 |

FOREIGN PATENT DOCUMENTS

| | | | |
|---|---|---|---|
| 2218908 | 11/1989 | United Kingdom | 607/114 |

OTHER PUBLICATIONS

"Omnipak" cold/hot support compress advertisement.

*Primary Examiner*—Jennifer Bahr
*Assistant Examiner*—David Ruddy
*Attorney, Agent, or Firm*—Alvin S. Blum

[57] ABSTRACT

A flexible heat transfer device for heating or cooling a surface such as the skin has an envelope formed from two double walled sheets, Each sheet contains within the double wall a first high thermal capacity material such as a freezing gel that is flexible when frozen for good surface contact. The space between the double walls contains a second high thermal capacity material that may have different physical properties than the first material. This may be in the form of a removable pouch insert that may be heated or cooled separately. The device is more versatile in its applications and provides for more prolonged heating and cooling.

20 Claims, 1 Drawing Sheet

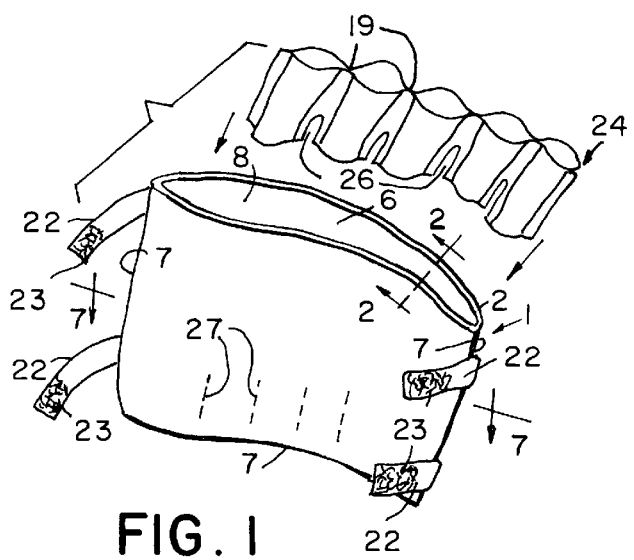
FIG. 1
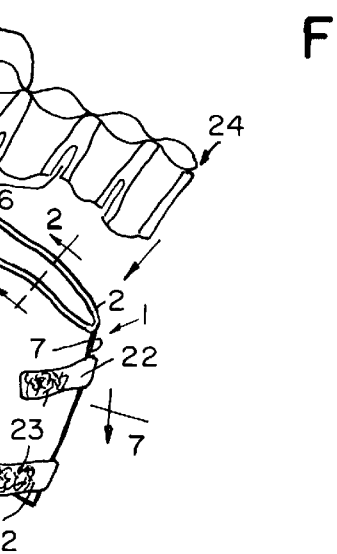
FIG. 2
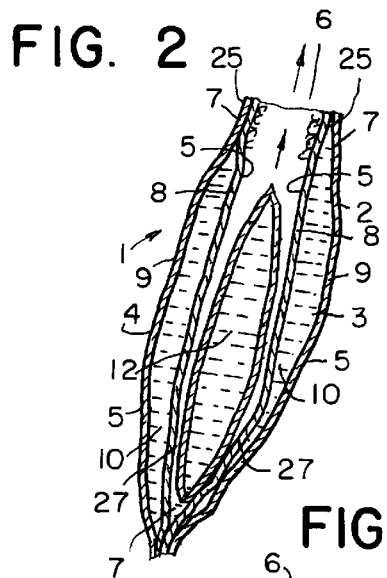
FIG. 4
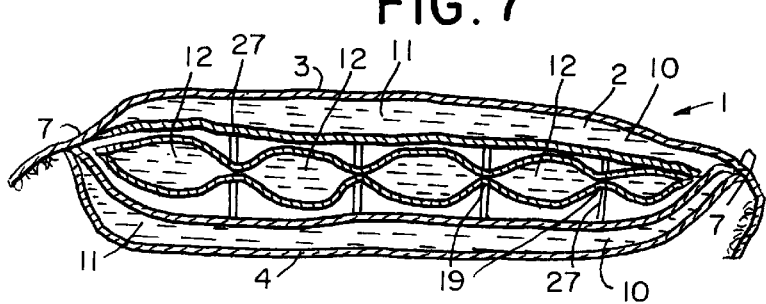
FIG. 7
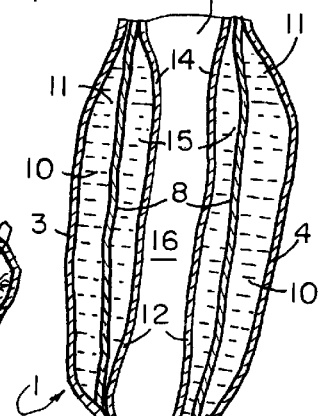
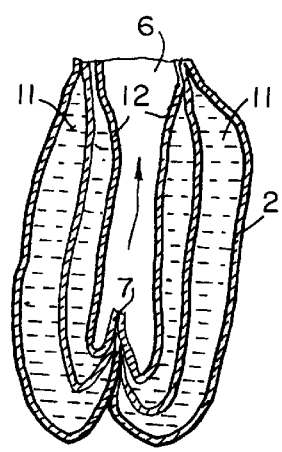
FIG. 3 FIG. 5
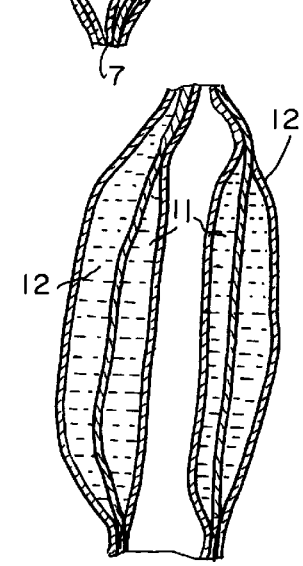
FIG. 6

HOT OR COLD APPLICATOR WITH INNER ELEMENT

BACKGROUND OF THE INVENTION

1. Field of the Invention

This invention relates to a reusable therapeutic device which may be used for cooling or heating and features a flexible bag which may be heated or cooled and then applied to a body part for thermal application with an inner element that enhances the thermal effects.

2. Description of the Prior Art

U.S. Pat. No. 4,592,358 issued Jun. 3, 1986 to Westplate provides a useful review of the patent literature in this art.

Despite the numerous advances that have been made in this art, people who need to apply heat or cold to the body for prolonged periods of time still find deficiencies in the available devices, because they don't provide relatively uniform temperature for relatively long periods of time, with the exception of the electric heating pads. When heat or cold is to be applied to the body surface, the temperature must not be so hot or cold as to be injurious or uncomfortable, while the total thermal capacity must be great enough to be therapeutically effective for a prolonged period of time.

SUMMARY OF THE INVENTION

It is accordingly an object of the invention to provide a cooling and/or heating applicator that is sufficiently flexible to conform to various body parts to make surface contact for effective heat transfer.

It is another object that the applicator provide heating and/or cooling at an effective temperature for a greatly prolonged period of time for optimal therapeutic benefit.

It is another object that the device be reversible so that the surface properties may be altered in at least one alternative embodiment.

It is yet another object that the device have a removable inner portion that may be separately heated or cooled in an alternative embodiment of the invention.

The invention comprises a flexible, conformable heat or cold pack having an envelope of a first high heat capacity material surrounding a second high heat capacity material for enhanced and more prolonged application of heating or cooling to a surface.

These and other objects, advantages and features of the invention will become more apparent when the detailed description is studied in conjunction with the drawings, in which like elements are designated by the same reference characters in the various figures.

BRIEF DESCRIPTION OF THE DRAWINGS

FIG. 1 is a perspective view of the invention with a removable refrigerant pouch ready to be inserted.

FIG. 2 is a sectional view taken through line 2—2 of FIG. 1 with pouch inserted.

FIG. 3 is a sectional view, as in FIG. 2, of another embodiment of the invention with a non-removable inner high thermal capacity material.

FIG. 4 is a sectional view, as in FIG. 2, of another embodiment of the invention with reversible inner and outer high thermal capacity materials.

FIG. 5 is a sectional view of the embodiment of FIG. 4 partially everted.

FIG. 6 is a sectional view of the embodiment of FIG. 4 completely everted.

FIG. 7 is a sectional view taken through line 7—7 of FIG. 1.

DETAILED DESCRIPTION OF PREFERRED EMBODIMENTS

Referring now first to FIGS. 1, 2 and 7, the embodiment of the invention shown here comprises a flexible heat transfer device 1 that conforms readily to the irregular surface of a body part so as to provide good surface contact for effective thermal transfer for heating or cooling. End straps 22 with hook and loop fasteners 23 permit the device to be wrapped around an arm, for example, and secured in place by the straps. The device 1 includes an outer envelope 2 formed of two double-walled sheets 3, 4 having broad faces 5. The sheets 3, 4 are joined together on 3 edges 7 and unjoined on one edge 6. Each double-walled sheet 3, 4 is formed of an inner panel 8 and an outer panel 9 sealed along all their edges 6, 7 to define therebetween a volume 10. The volumes 10 contain a first high thermal capacity material 11 such as one of the freezing gels well known in the art, such as that disclosed by U.S. Pat. No. 4,324,111 which changes state from liquid to slush at around zero degrees centigrade and requires considerable heat energy as it warms through this change of state to serve as an artificial ice that is not rigid. U.S. Pat. No. 5,314,005 discusses other materials for this purpose including some that may be heated in a microwave oven for use as hot packs.

The envelope so formed is open at the edge 6 to permit the insertion of a flexible pouch 24. The pouch 24 and the envelope are formed of thin flexible liquid-impermeable web such as plastic film. The thickness has been exaggerated for illustrative purposes.

The pouch 24 contains a second high thermal capacity material 12. After inserting the pouch 24 through the open side 6 of the envelope into the space 13 defined by the inner panels 8, the open side 6 may be closed by a releasable closure 25 which may be hook and loop, snaps, zipper, or the like.

Multiple pouches 24 may be provided so that one is being used in the envelope while others are being chilled or heated.

The pouch 24 may be segmented as shown to make it more flexible and to maintain a flatter shape for insertion in the envelope by seams 19 sealing together the two flexible webs 14 that make up the outer wall of the pouch. The seams 19 may be provided with notches 26 that cooperate with short partitions 27 connecting the inner panels 8. This stabilizes the pouch within the envelope.

The high thermal capacity material 12 in the pouch may be identical to, or different than the material 11 in the envelope walls. It may even be rigid when frozen such as plain water, since segmentation provides some flexibility.

The materials 11 and 12 may be selected on the basis of their particular physical properties to enhance the utility of the device. Those properties include, but are not limited to, heat of fusion, heat capacity, thermal conductivity, temperature of transition from liquid to solid, rigidity in the solid phase, reaction to microwave radiation, vapor pressure and boiling point.

Thermal conductivity of the material 11 is important in the rate of transfer of heat to or from the insert or pouch 24. By acting as a partial insulator, it can prolong the cooling effect and also prevent a very cold or hot insert from injuring the skin, while maintaining a relatively uniform surface temperature. The envelope 2 may also be used without the pouch, as desired.

Referring now to FIG. 3, a heat transfer device 1 is shown in which the two double-walled sheets 3, 4 are sealed on all edges 6, 7 with a sealed inner space 13 defined by the two inner panels 8 containing the second high thermal capacity material 12 and the volumes between the double walls of each sheet containing the first high thermal capacity material 11.

FIGS. 4–6 show another embodiment of the invention in which the entire device may be turned inside out like a reversible jacket. As shown in the first mode of operation in FIG. 4, the device 1 is formed of two double walled sheets 3, 4 containing in the volumes 10 between outer panels 9 and inner panels 8 a first high thermal capacity material 11. The two sheets are sealed on three edges and not sealed on edge 6. The space between the two sheets is divided into three compartments by two webs 14. Each web 14 is sealed on all its edges to one or the other inner panel 8 to define therebetween a sealed compartment 15 containing therein the second high thermal capacity material 12. The third compartment 16 defined by the two webs 14 is open at the edge 6, and is empty.

As shown in FIGS. 5 and 6, the envelope 2 may be everted or turned inside out to the configuration of FIG. 6 in which the second material 12 is on the outside enveloping the first material 11 on the inside. This embodiment may be useful when the different physical properties of materials 11 and 12 may be more useful on the outside for certain applications, making a single device more versatile.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

What is claimed is:

1. A heat transfer device for heating and cooling a surface, the device comprising:
    an envelope formed of first and second double-walled sheets, the sheets having broad faces and joined together on at least all but one edge;
    each double-walled sheet formed of an inner and an outer panel of flexible, liquid-impermeable webbing, the panels joined together on all edges to define therebetween a volume that contains a first high thermal capacity material that is not rigid at about zero degrees centigrade; and
    a space defined by the inner panels of the two double-walled sheets, the space containing therein a second high thermal capacity material, the space being separate from said volume so that the first and second high thermal capacity materials cannot mix.

2. The device according to claim 1, in which the first and second high thermal capacity materials have different physical properties.

3. The device according to claim 2, in which the double-walled sheets are joined together on all but one edge, and the space is divided into three compartments by two flexible webs, each web having all edges thereof joined to an inner panel of one or the other of the sheets, the space between the two webs being empty of the second material and each compartment defined by a web and an inner panel containing the second material, such that the envelope may be optionally everted to position the second material outwardly.

4. The device according to claim 1, in which the double-walled sheets are joined together on all but one edge, and the space is divided into three compartments by two flexible webs, each web having all edges thereof joined to an inner panel of one or the other of the sheets, the space between the two webs being empty of the second material and each compartment defined by a web and an inner panel containing the second material, such that the envelope may be optionally everted to position the second material outwardly.

5. The device according to claim 1 further comprising a flexible pouch having sealed therein the second material, the pouch adapted for removable containment within the space.

6. The device according to claim 5, in which the pouch is segmented.

7. The device according to claim 5, in which all but one edge of the two sheets are permanently sealed together and the one edge is releasably closed for removably retaining the flexible pouch within the space.

8. The device according to claim 6, in which all but one edge of the two sheets are permanently sealed together and the one edge is releasably closed for removably retaining the flexible pouch within the space.

9. A flexible therapeutic heat transfer device for heating or cooling a body surface, the device comprising:
    an envelope formed of first and second double-walled sheets, the sheets having broad faces, the two sheets fixedly joined together on all but one edge;
    each double-walled sheet formed of an inner and an outer panel of flexible, liquid-impermeable, webbing, the panels joined together on all edges thereof to define therebetween a volume that contains a first high thermal capacity material that is not rigid at about zero degrees centigrade;
    a space defined by the inner panels of the two double-walled sheets, the all but one fixedly joined edges and the one edge, the space containing therein a flexible pouch containing a second high thermal capacity material sealed therein, said space being separate from said volume so that the first and second high thermal capacity materials cannot mix; and
    a releasable closure means attached to the one edge adapted for removably retaining the pouch within the space.

10. The device according to claim 9, in which the first and second high thermal capacity materials have different physical properties.

11. The device according to claim 10, in which the pouch is segmented.

12. The device according to claim 1, in which the first high thermal capacity material is a freezing gel.

13. The device according to claim 9, in which the first high thermal capacity material is a freezing gel.

14. The device according to claim 1, in which all of the edges of the first and second double walled sheets are permanently joined together.

15. A heat transfer device for heating and cooling a surface, the device comprising:
    an envelope formed of first and second double-walled sheets, the sheets having broad faces and joined together on at least all but one edge;
    each double-walled sheet formed of an inner and an outer panel of flexible, liquid-impermeable webbing, the panels joined together on all edges to define therebetween a volume that contains a first freezing gel; and
    a space defined by the inner panels of the two double-walled sheets, the space containing therein a second freezing gel, the space being separate from said volume so that the first and second freezing gels cannot mix.

16. The device according to claim 15, in which the double-walled sheets are joined together on all but one edge, and the space is divided into three compartments by two flexible webs, each web having all edges thereof joined to an inner panel of one or the other of the sheets, the space between the two webs being empty of the second freezing gel and each compartment defined by a web and an inner panel containing the second freezing gel, such that the envelope may be optionally everted to position the second gel outwardly.

17. The device according to claim 15, in which the double-walled sheets are joined together on all but one edge, and the space is divided into three compartments by two flexible webs, each web having all edges thereof joined to an inner panel of one or the other of the sheets, the space between the two webs being empty of the second gel and each compartment defined by a web and an inner panel containing the second gel, such that the envelope may be optionally everted to position the second gel outwardly.

18. A flexible therapeutic heat transfer device for heating or cooling a body surface, the device comprising:

an envelope formed of first and second double-walled sheets, the sheets having broad faces, the two sheets fixedly joined together on all but one edge;

each double-walled sheet formed of an inner and an outer panel of flexible, liquid-impermeable webbing, the panels joined together on all edges thereof to define therebetween a volume that contains a first freezing gel;

a space defined by the inner panels of the two double-walled sheets, the all but one fixedly joined edges and the one edge, the space containing therein a flexible pouch containing a second freezing gel sealed therein, said space being separate from said volume so that the first and second freezing gels cannot mix; and a releasable closure means attached to the one edge adapted for removably retaining the pouch within the space.

19. The device according to claim 18, in which the first and second freezing gels have different physical properties.

20. The device according to claim 18, in which the pouch is segmented.

* * * * *